United States Patent
Spurr

(10) Patent No.: US 11,039,982 B1
(45) Date of Patent: Jun. 22, 2021

(54) MEDICATION DELIVERY DEVICE

(71) Applicant: Suzanne L. Spurr, Linthicum Heights, MD (US)

(72) Inventor: Suzanne L. Spurr, Linthicum Heights, MD (US)

(73) Assignee: Suzanne L. Spurr, Pharm.D. LLC, Linthicum Heights, MD (US)

( * ) Notice: Subject to any disclaimer, the term of this patent is extended or adjusted under 35 U.S.C. 154(b) by 643 days.

(21) Appl. No.: 15/842,327

(22) Filed: Dec. 14, 2017

(51) Int. Cl.
*A61J 1/20* (2006.01)
*A61M 11/00* (2006.01)
*A61M 31/00* (2006.01)

(52) U.S. Cl.
CPC .......... *A61J 1/2093* (2013.01); *A61J 1/2027* (2015.05); *A61J 1/2037* (2015.05); *A61M 11/008* (2014.02); *A61M 31/00* (2013.01); *A61M 2210/0618* (2013.01)

(58) Field of Classification Search
CPC ...... A61J 1/2093; A61J 1/2027; A61J 1/2037; A61M 11/008; A61M 31/00; A61M 2210/0618
See application file for complete search history.

(56) References Cited

U.S. PATENT DOCUMENTS

| | | | |
|---|---|---|---|
| 3,340,869 A | 9/1967 | Bane | |
| 7,306,129 B2 | 12/2007 | Swiss et al. | |
| 8,485,398 B2 | 7/2013 | Kneer | |
| 2006/0079851 A1 | 4/2006 | Guerrieri | |
| 2008/0177246 A1* | 7/2008 | Sullivan | A61M 15/0031 604/520 |
| 2012/0017898 A1* | 1/2012 | Moller | A61M 11/008 128/203.12 |
| 2012/0074001 A1* | 3/2012 | Genosar | A61J 1/2093 206/219 |

FOREIGN PATENT DOCUMENTS

| | | |
|---|---|---|
| EP | 0170262 A2 | 2/1986 |
| WO | 2016032814 A1 | 3/2016 |

\* cited by examiner

*Primary Examiner* — Phillip A Gray
(74) *Attorney, Agent, or Firm* — Cramer Patent & Design, PLLC; Aaron R. Cramer

(57) ABSTRACT

A medication delivery device involves an ampule having a receptacle base secured to a tab-shaped cap. The exterior surface between the base and cap is scored to permit a user to twist the cap in a first direction thereby severing the cap from the base and permitting medication secured within the base to be accessed. Adjacent the cap on an interior of the ampule is a unidirectional valve which moderates the ejection of fluid into at least two (2) doses. An exterior portion of the base has a surface suitable for any desired indicia.

9 Claims, 6 Drawing Sheets

MEDICATION DELIVERY DEVICE

RELATED APPLICATIONS

Not applicable.

FIELD OF THE INVENTION

The present invention relates generally to the field of medication delivery devices for use in emergency situations.

BACKGROUND OF THE INVENTION

There are a wide variety of present day medications that are delivered by nasal spray. One (1) of these receiving much media attention of late, is that of NARCAN® (naloxone HCL) nasal spray which is used to treat opioid overdoses or possible opioid overdoses. This medication is provided in a single dose applicator that is ready to use.

Unfortunately, due to current proprietary licenses, regulations, and other legal restrictions, such medication is only available at a high cost, even though the actual medication itself is generally readily available at a much lower cost. Due to these costs, NARCAN® and other similar medicines delivered through the nasal cavity is not readily available to all, resulting in a lower quality of life, and perhaps even death for some individuals. Accordingly, there exists a need for a means by which various medications can be packaged in a readily available standard means for lower costs and greater availability. The development of the two-stage spray medication delivery device for nasal cavities fulfills this need.

SUMMARY OF THE INVENTION

The principles of the present invention provide for a medication delivery device that includes a vial body and a cap removably attached to the vial body. Such a vial body includes a first reservoir, a first activation area located on an external surface of the vial body and aligned with the first reservoir, a bicuspid valve in fluid communication with the first reservoir, a second reservoir in fluid communication with the bicuspid valve, a second activation area located on the external surface of the vial body and aligned with the second reservoir, and an applicator tip located at a first end and in fluid communication with the second reservoir. In certain embodiments, the vial body can include a fill area located at a second end, opposite the applicator tip, and sealed with a crimped end. The cap is removably affixed to both the vial body and the applicator tip. In other embodiments, a first capacity of the first reservoir is equal to a second capacity of the second reservoir.

It is therefore an object of the present invention to provide that the first reservoir is capable of retaining an amount of first fluid contents therein, and the second reservoir is capable of retaining an amount of second fluid contents therein. Activation of the first activation area advances the first fluid contents through the bicuspid valve towards the second reservoir and the second fluid contents within the second reservoir are advanced towards the applicator tip for dispensing thereof. A subsequent activation of the second activation area advances the first fluid contents towards the applicator tip for dispensing thereof.

It is a further object of the present invention to provide such a cap to be removably affixed to the applicator tip with a first seamed connection. Also, the cap can be removably affixed to the vial body via a pair of connection tabs, each with a second seamed connection. The connection tabs are located on either side of the applicator tip.

It is another object of the present invention to provide a first information area located on the external surface of said vial body. The first information area is preferably removably attached to the vial body subjacent to the first activation area. A second information area is also removably attached to the external surface of the vial body.

It is still another object of the present invention to provide that the first activation area comprises a first embossed feature and the second activation area comprises a second embossed feature.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

Figure 1:
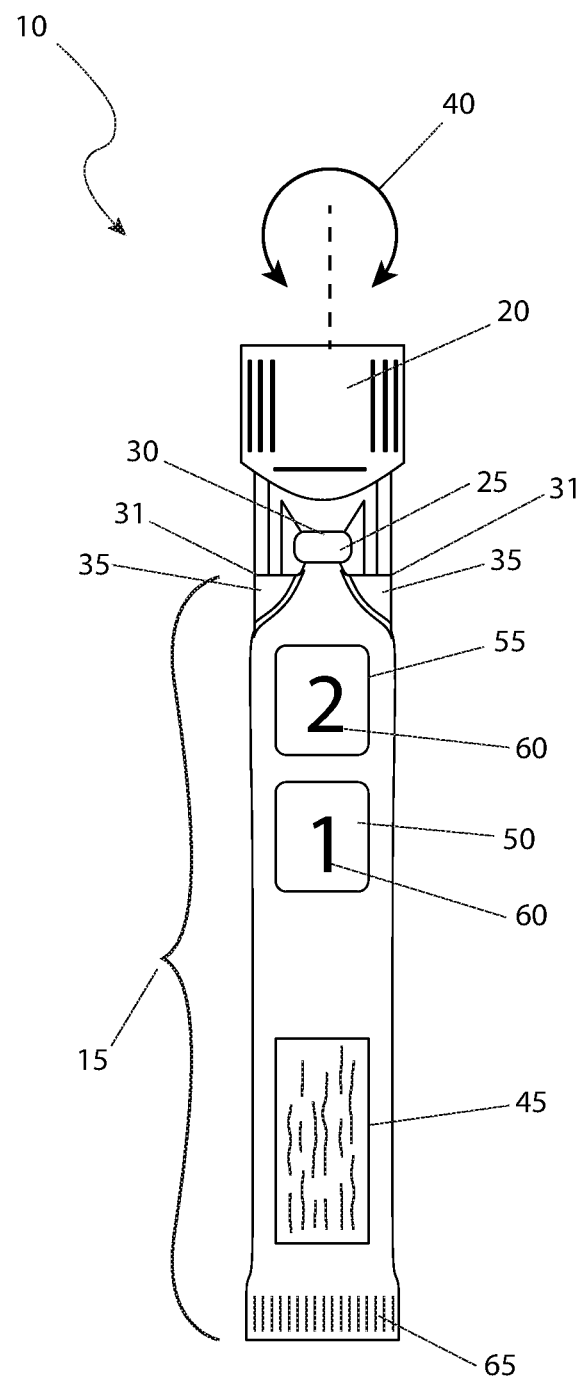
FIG. 1 is a front view of the medication delivery device 10, according to the preferred embodiment of the present invention.

DESCRIPTIVE KEY 10 medication delivery device
11 alternate medication delivery device
15 vial body
20 snap-off one-time cap
25 applicator tip
30 first seamed connection
31 second seamed connection
35 connection tab
40 rotational travel path
45 first information indicia area
50 first finger press activation area
55 second finger press activation area
60 embossed indicia
65 fill access area
70 second information indicia area
75 first reservoir
80 second reservoir
85 bicuspid valve
90 reservoir neck
95 first travel path
100 second travel path
105 patient
110 care provider
115 first nostril
120 second nostril

DETAILED DESCRIPTION OF THE PREFERRED EMBODIMENT

The best mode for carrying out the invention is presented in terms of its preferred embodiment, herein depicted within FIGS. 1 through 5. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one (1) particular configuration shall be shown and described for purposes of clarity and disclosure and not by way of limitation of scope. All of the implementations described below are exemplary implementations provided to enable persons skilled in the art to make or use the embodiments of the disclosure and are not intended to limit the scope of the disclosure, which is defined by the claims.

The terms "a" and "an" herein do not denote a limitation of quantity, but rather denote the presence of at least one (1) of the referenced items.

Referring now to FIG. 1, a front view of the medication delivery device 10 for nasal cavities 115,120, according to the preferred embodiment of the present invention is disclosed. The medication delivery device 10 (herein also described as the "device") 10, includes a vial body 15 that can deliver medicine is two (2) stages, which will be described in greater detail herein below. It is preferred that the overall length of the device is approximately two-and-a-half inches (2½ in.).

The device 10 is provided with a snap-off one-time cap 20 on its uppermost end which covers an applicator tip 25. The snap-off one-time cap 20 is attached via a first seamed connection 30 at the applicator tip 25 and with a pair of second seamed connections 31 each at one (1) of a pair of (2) connection tabs 35. The snap-off one-time cap 20 is removed by grasping the vial body 15 in one (1) hand and rotating the snap-off one-time cap 20 about the central axis of the vial body 15 in a rotational travel path 40. This rotation will break both the first seamed connection 30 and pair of second seamed connections 31 to remove the snap-off one-time cap 20 from the applicator tip 25 and connection tabs 35, which remain with the vial body 15. This action is performed immediately prior to usage of the device 10 in order to maintain sterile conditions. Additionally, the action produces a smooth applicator tip 25 free from sharp protrusions. It is appreciated that the first seamed connection 30 and pair of second seamed connections 31 are perforated portions of the common material of the vial body 15 and snap-off one-time cap 20, but other seamed connections may be appreciated.

The vial body 15 is provided with a first information indicia area 45 for purposes of conveying medical information and dosage requirements including but not limited to: drug, strength, lot, expiration date, brand name, and manufacturer. The first information indicia area 45 may be a separate application of a Mylar™ (or other biaxially-oriented polyethylene terephthalate (BoPET)) label, which is rub and removal resistant, although other styles of labeling such as paper, embossing, vinyl, thermal, or the like may be used with equal effectiveness. As such, the particular method of labeling used with the first information indicia area 45 is not intended to be a limiting factor of the present invention. The balance of the vial body 15 is provided with a first finger press activation area 50 and a second finger press activation area 55, both of which are prominently marked with embossed indicia 60. Further description on the usage of the first finger press activation area 50 and the second finger press activation area 55 will be provided herein below.

All components as shown in FIG. 1 with the exception of separate first information indicia area 45 would be made of sterile polymers such as low-density polyethylene (LDPE) in a one-piece molding operation. The device 10 would be filled with liquid medication through a fill access area 65 and sealed with the application of heat. The actual color of all components may vary per application, however for emergency application where time is of the essence, the color red would be viewed as advantageous. However, the use of any particular color is not intended to be a limiting factor of the present invention. Finally, while the use of the device 10 is viewed as particularly beneficial when administering opioid antidotes such a NARCAN® (naloxone HCl), the teachings of the device 10 can be used with any medication delivered via the nasal cavity in an atomized state, nebulized state, or any other dispensed state. As such, the use of the device 10 with any particular type of medication is not intended to be a limiting factor of the present invention.

Figure 2:
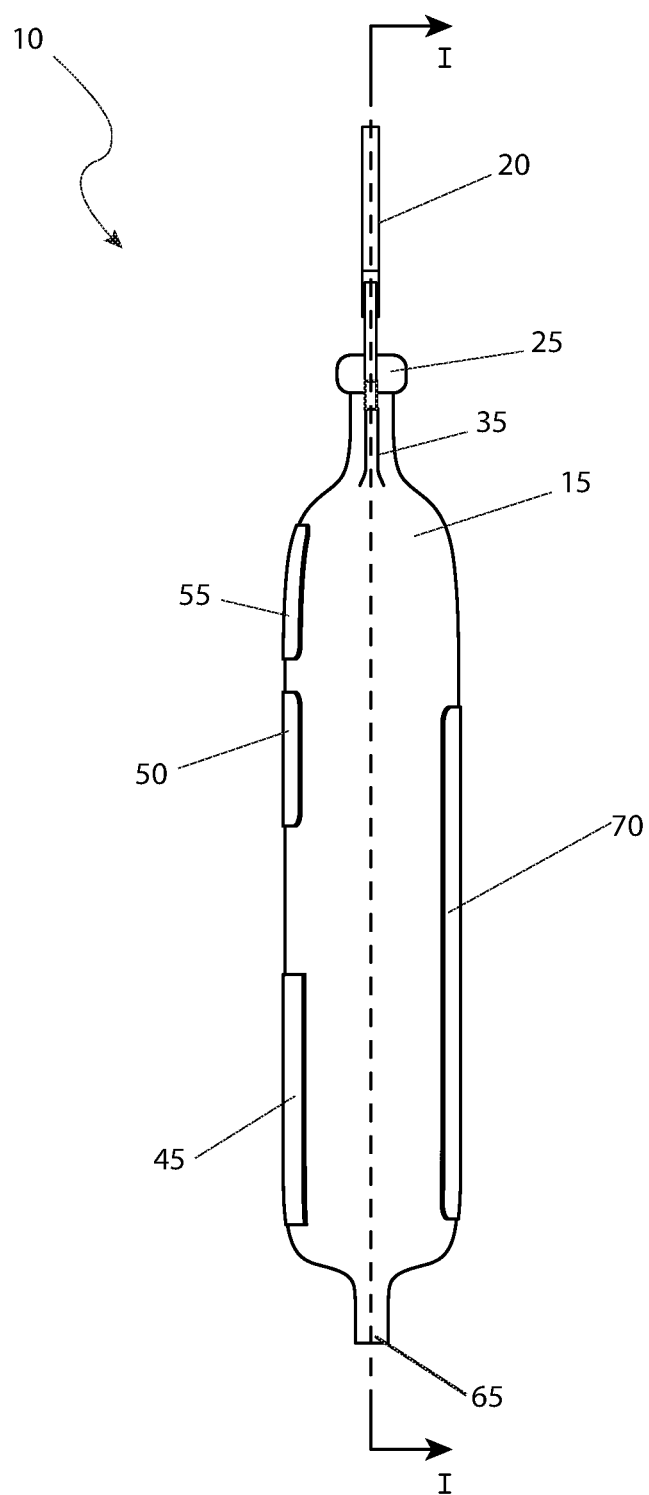
FIG. 2 is a side view of the medication delivery device 10, according to the preferred embodiment of the present invention.
Figure 6:
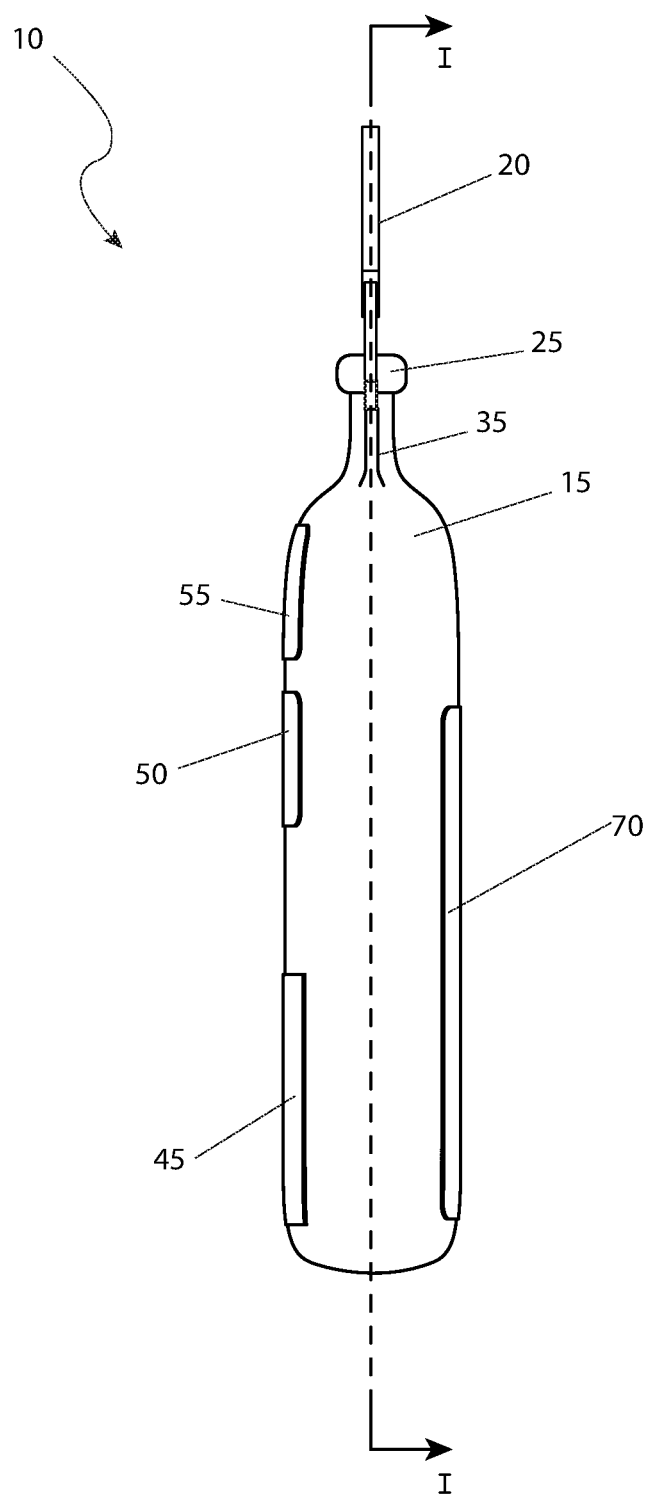

Referring now to FIG. 2, a side view of the device 10, according to the preferred embodiment of the present invention is depicted. This figure clearly depicts the tubular nature of the device 10, with the snap-off one-time cap 20 and applicator tip 25 located at the distal end and the fill access area 65 located at the proximal end during usage. Usage instructions will be provided herein below. An alternate device 11 may also be pre-filled and have a continuous shape and not have a crimped seal sealing off the fill access area 65 (see FIG. 6).

The prominent nature of the first finger press activation area 50 and second finger press activation area 55 are visible due to their embossed features, thus making them easy and sure to use in a wide variety of situations such as emergency, duress, low-light, and/or physically limiting situations such as wet hands, limited nasal opening access or the like. The first information indicia area 45 is visible below the first finger press activation area 50. Additionally, a second information indicia area 70 is visible on the opposite side of the vial body 15. The second information indicia area 70 provides the opportunity to include additional data on the device 10, not possible due to the limited area on the first information indicia area 45. As before, the second information indicia area 70 is for purposes of conveying medical information and dosage requirements including but not limited to: drug, strength, lot, expiration date, brand name, and manufacturer. The second information indicia area 70 may be a separate application of a Mylar™ label, which is rub and removal resistant, although other styles of labeling such as paper, embossing, vinyl, thermal, or the like may be used with equal effectiveness. As such, the particular method of labeling used with the second information indicia area 70 is not intended to be a limiting factor of the present invention.

Figure 3:
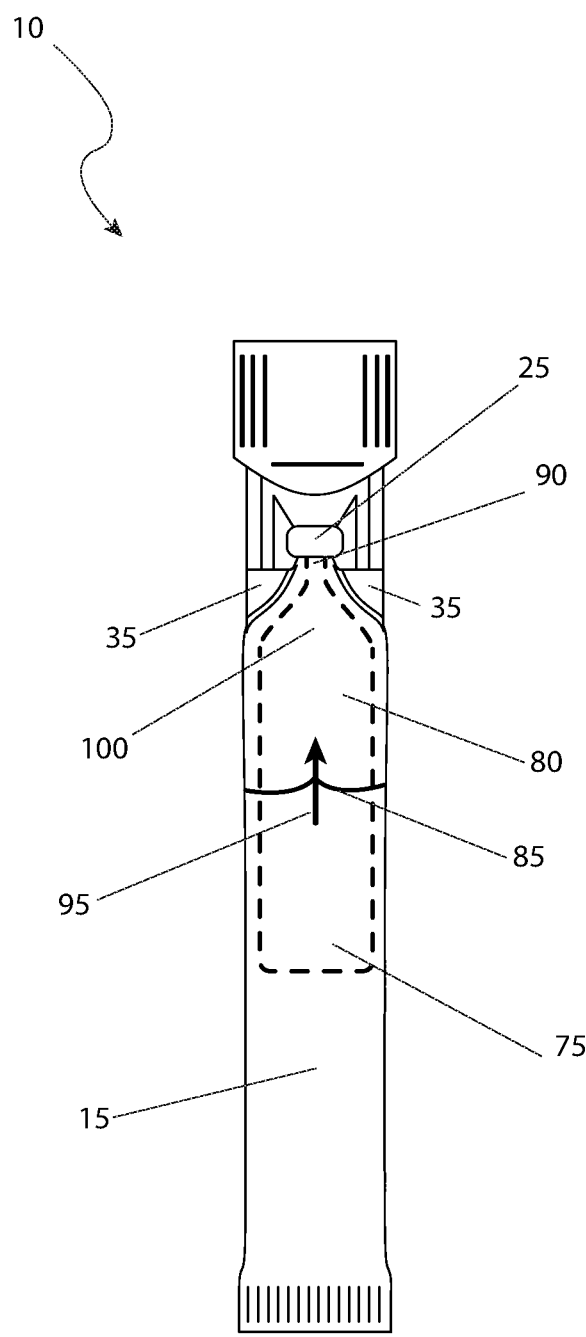
FIG. 3 is a sectional view of the medication delivery device 10, as seen along a line I-I, as shown in FIG. 2, according to the preferred embodiment of the present invention.

Referring next to FIG. 3, a sectional view of the device 10, as seen along a line I-I, as shown in FIG. 2, according to the preferred embodiment of the present invention is shown. A first reservoir 75 and a second reservoir 80 are separated by a bicuspid valve 85. The total volume provided by both the first reservoir 75 and the second reservoir 80 can vary per specific model and intended usage of the device 10, but a typical version is envisioned to hold approximately one-point-one milliliter (1.1 ml) or one-point-one cubic centimeter (1.1 cm$^3$), with half of the amount in first reservoir 75 and the other half in second reservoir 80. It is noted that the volume contained within the vial body 15 can vary without changing the overall dimensions of the vial body 15.

The second reservoir 80 is located immediately subjacent to and in fluid communication with the applicator tip 25 via a reservoir neck 90. It is noted that the first reservoir 75 aligns with the first finger press activation area 50 (as shown in FIG. 1) and the second reservoir 80 aligns with the second finger press activation area 55 (as shown in FIG. 1). Thus, when pressure is applied to the first reservoir 75, the medication present herein is transferred through the bicuspid valve 85 as indicated by a first travel path 95. Equalization of pressure then causes the medication present in the second reservoir 80 to be transferred to the applicator tip 25 via the reservoir neck 90 along a second travel path 100. Sequentially, when the second finger press activation area 55 is pressed, the liquid medication contained within the second reservoir 80 is transferred to the applicator tip 25 via the reservoir neck 90 along a second travel path 100. Backflow into the first reservoir 75 is prevented by the one-way nature of the bicuspid valve 85. Further instructions on the administration and usage of the device 10 will be provided herein below.

Figure 4:
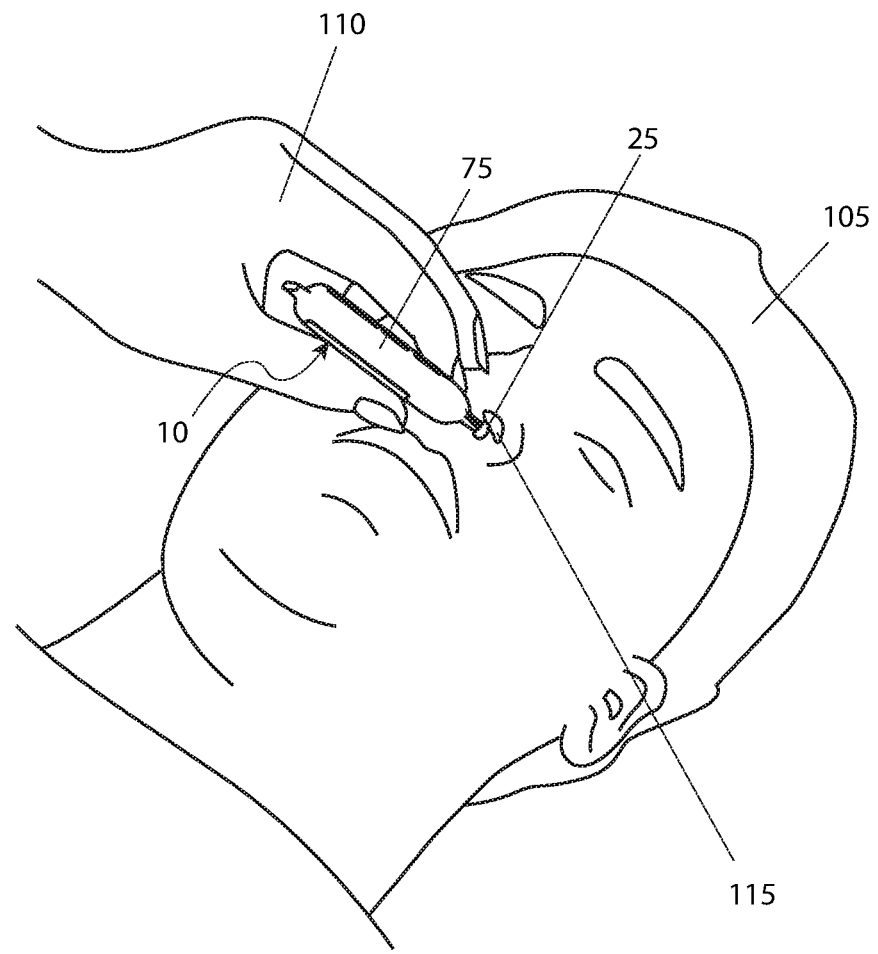
FIG. 4 is a perspective view of the medication delivery device 10, shown in a first utilized state, according to the preferred embodiment of the present invention.

Referring now FIG. 4, a perspective view of the device 10, shown in a first utilized state, according to the preferred embodiment of the present invention is disclosed. A patient 105 in need of medication delivered by the device 10 is present. A care provider 110 removes the snap-off one-time cap 20 (as shown in FIG. 1), and places the applicator tip 25 within a first nostril 115 of the patient 105. The care provider 110 then applies pressure (between the thumb and forefinger) to the first reservoir 75, forcing the medication present through the bicuspid valve 85 (as shown in FIG. 3) and into the reservoir neck 90 (as shown in FIG. 3). The medication present in the second reservoir 80 (as shown in FIG. 3) is then transferred to the applicator tip 25 via the reservoir neck 90 and dispensed into the patient's nasal cavity for absorption. Additional description of the entire usage process will be provided herein below in the operation of the preferred embodiment.

Figure 5:
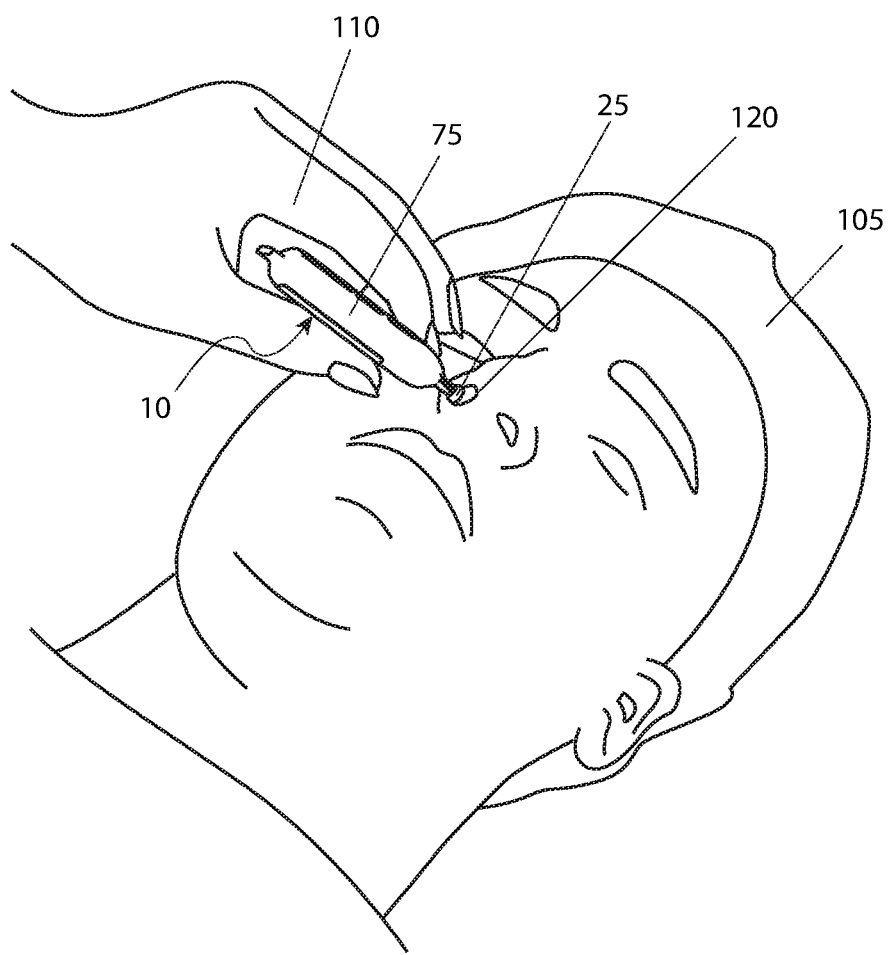
FIG. 5 is a perspective view of the medication delivery device 10, shown in a second utilized state, according to the preferred embodiment of the present invention; and, FIG. 6 is a front view of an alternate medication delivery device 11, according to an alternate embodiment of the present invention.

Referring finally to FIG. 5, a perspective view of the device 10, shown in a second utilized state, according to the preferred embodiment of the present invention. In a sequential manner, a patient 105 in need of additional medication beyond that described in FIG. 4 is present. The care provider 110 places the applicator tip 25 within a second nostril 120 of the patient 105. The care provider 110 then applies pressure (between the thumb and forefinger) to the second reservoir 80, forcing the medication present into the reservoir neck 90 (as shown in FIG. 3) and dispensed into the patient's nasal cavity for absorption. Additional description of the entire usage process will be provided herein below in the operation of the preferred embodiment.

The preferred embodiment of the present invention can be utilized by the common user in a simple and effortless manner with little or no training. It is envisioned that the device 10 would be constructed in general accordance with FIG. 1 through FIG. 5. The user would procure the device 10 through normal pharmaceutical channels with emphasis on nature of the medication contained within the device 10 and likelihood of usage in an emergency situation. Additionally, suitable training on usage instructions and applicable application situations would be obtained by the care provider 110.

During utilization of the device 10, the following procedure would be initiated: the care provider 110 would remove the snap-off one-time cap 20 by applying force along a rotational travel path 40 to break the first seamed connection 30 and second seamed connections 31; the applicator tip 25 would be placed in a first nostril 115 of the patient 105; pressure would be applied to the first finger press activation area 50 (ejecting half of the total contained contents of the device 10); contents would be absorbed in the nasal cavity of the patient 105; a suitable waiting time period (dependent on the medical situation) would occur; the care provider 110 would summon additional emergency help (through dialing of "911"); should additional medication be required, the care provider 110 would place the applicator tip 25 in the second nostril 120 of the patient 105; pressure would be applied to the second finger press activation area 55 (ejecting the remaining half of the total contained contents of the device 10); contents would be absorbed in the nasal cavity of the patient 105; an additional suitable waiting time period (dependent on the medical situation) would occur. Should the total contents of the first reservoir 75 and second reservoir 80 not be emptied, the care provider 110 would press both the first finger press activation area 50 and the second finger press activation area 55 while the applicator tip 25 is in either the first nostril 115 or the second nostril 120 to ensure all medication is available to the patient 105.

Such procedure describes the usage cycle of one (1) device 10. Other medical procedures such as transport to hospital, administration of cardiopulmonary resuscitation (CPR), administration of another dosage via another device 10, or the like may be necessary. Such procedures are beyond the teachings of the present invention and do not limit the usage of the device 10. After use of the device 10, it is disposed of following suitable medical waste disposal processes.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

The invention claimed is:

1. A medication delivery device, comprising:
   a vial body, comprising:
     a first reservoir;
     a first activation area located on an external surface of said vial body and aligned with said first reservoir;
     a bicuspid valve in fluid communication with said first reservoir;
     a second reservoir in fluid communication with said bicuspid valve;
     a second activation area located on said external surface of said vial body and aligned with said second reservoir;
     an applicator tip located at a first end thereof and in fluid communication with said second reservoir;
     a fill area located at a second end thereof, opposite said applicator tip, and sealed with a crimped end;
   a cap removably affixed to said vial body and covering said applicator tip; and
   a first information area located on said external surface of said vial body;
     wherein said first information area is removably attached to said vial body subjacent said first activation area;
     wherein said first reservoir is capable of retaining an amount of first fluid contents therein;

wherein said second reservoir is capable of retaining an amount of second fluid contents therein;
wherein activation of said first activation area advances said first fluid contents through said bicuspid valve towards said second reservoir and said second fluid contents within said second reservoir are advanced towards said applicator tip for dispensing thereof;
wherein a subsequent activation of said second activation area advances said first fluid contents towards said applicator tip for dispensing thereof;
wherein said cap is removably affixed to said applicator tip and is removably affixed to said vial body to a pair of connection tabs located on either side of said applicator tip;
wherein a first capacity of said first reservoir is equal to a second capacity of said second reservoir;
wherein said first activation area comprises a first embossed feature; and
said second activation area comprises a second embossed feature.

2. The device of claim 1, wherein said cap is affixed to said applicator tip with a first seamed connection.

3. The device of claim 2, wherein said cap is affixed to said pair of connection tabs via a pair of second seamed connections.

4. The device of claim 1, further comprising a second information area located on said external surface of said vial body.

5. The device of claim 4, wherein said second information area is removably attached to said vial body.

6. A medication delivery device, comprising:
a vial body, comprising:
a first reservoir;
a first activation area located on an external surface of said vial body and aligned with said first reservoir;
a bicuspid valve in fluid communication with said first reservoir;
a second bicuspid reservoir in fluid communication with said bicuspid valve;
a second activation area located on said external surface of said vial body and aligned with said second reservoir;
an applicator tip located at a first end thereof and in fluid communication with said second reservoir;
a cap removably affixed to said vial body and covering said applicator tip;
a first information area located on said external surface of said vial body;
wherein said first information area is removably attached to said vial body subjacent said first activation area;
wherein said first reservoir is capable of retaining an amount of first fluid contents therein;
wherein said second reservoir is capable of retaining an amount of second fluid contents therein;
wherein activation of said first activation area advances said first fluid contents through said bicuspid valve towards said second reservoir and said second fluid contents within said second reservoir are advanced towards said applicator tip for dispensing thereof;
wherein a subsequent activation of said second activation area advances said first fluid contents towards said applicator tip for dispensing thereof;
wherein said cap is removably affixed to said applicator tip and is removably affixed to said vial body to a pair of connection tabs located on either side of said applicator tip;
wherein said cap is affixed to said pair of connection tabs via a pair of second seamed connections;
wherein said first activation area comprises a first embossed feature; and
said second activation area comprises a second embossed feature.

7. The device of claim 6, further comprising a second information area located on said external surface of said vial body.

8. The device of claim 7, wherein said second information area is removably attached to said vial body.

9. The device of claim 6, wherein a first capacity of said first reservoir is equal to a second capacity of said second reservoir.

* * * * *